(12) United States Patent
André et al.

(10) Patent No.: US 11,419,983 B2
(45) Date of Patent: Aug. 23, 2022

(54) TRANSPORT ASSEMBLY FOR A MEDICAMENT DELIVERY DEVICE AND A MEDICAMENT DELIVERY DEVICE COMPRISING THE SAME

(71) Applicant: SHL MEDICAL AG, Zug (CH)

(72) Inventors: Erika André, Saltsjö-Boo (SE); Pär Leander, Nacka (SE); Linda Odelberg, Ekerö (SE); Anders Holmqvist, Värmdö (SE)

(73) Assignee: SHL MEDICAL AG, Zug (CH)

( * ) Notice: Subject to any disclaimer, the term of this patent is extended or adjusted under 35 U.S.C. 154(b) by 272 days.

(21) Appl. No.: 16/630,377

(22) PCT Filed: Jul. 2, 2018

(86) PCT No.: PCT/EP2018/067777
§ 371 (c)(1),
(2) Date: Jan. 10, 2020

(87) PCT Pub. No.: WO2019/011689
PCT Pub. Date: Jan. 17, 2019

(65) Prior Publication Data
US 2020/0129696 A1    Apr. 30, 2020

(30) Foreign Application Priority Data

Jul. 12, 2017  (EP) .................................. 17180916

(51) Int. Cl.
*A61M 5/20* (2006.01)
*A61M 5/315* (2006.01)
*A61M 5/32* (2006.01)

(52) U.S. Cl.
CPC ...... *A61M 5/2033* (2013.01); *A61M 5/31501* (2013.01); *A61M 5/3202* (2013.01);
(Continued)

(58) Field of Classification Search
CPC ............ A61M 5/2033; A61M 5/31501; A61M 5/3202; A61M 2005/2073; A61M 2209/06; A61M 5/31571
(Continued)

(56) References Cited

U.S. PATENT DOCUMENTS

2010/0036318 A1* 2/2010 Raday .................... A61M 5/50
604/218
2014/0323982 A1* 10/2014 Lumme ............... A61M 5/3234
604/218
(Continued)

FOREIGN PATENT DOCUMENTS

CN   105246528 A   1/2016
EP   2799100 A2   11/2014
(Continued)

OTHER PUBLICATIONS

International Search Report and Written Opinion for Int. App. No. PCT/EP2018/067777, dated Jul. 25, 2018.

*Primary Examiner* — Bhisma Mehta
*Assistant Examiner* — Nidah Hussain
(74) *Attorney, Agent, or Firm* — McDonnell Boehnen Hulbert & Berghoff LLP (57) ABSTRACT

A transport assembly for shipping components of a medicament delivery device to final assembly is presented, where the transport assembly has a plunger rod, a first resilient member configured to bias the plunger rod, an elongated plunger rod holder configured to receive the plunger rod, a transport securing sleeve configured to receive a portion of the plunger rod holder, and configured to move axially from a first position relative to the plunger rod holder in which the transport securing sleeve prevents the plunger rod holder to disengage from the plunger rod to a second position located distally relative to the first position, enabling disengagement of the plunger rod holder from the plunger rod, a rear end
(Continued)

cap, and a second resilient member configured to bear against the rear end cap and configured to bias the transport securing sleeve in the proximal direction away from the second position.

19 Claims, 6 Drawing Sheets

(52) U.S. Cl.
CPC .............. *A61M 2005/2006* (2013.01); *A61M 2005/2073* (2013.01); *A61M 2209/06* (2013.01)

(58) Field of Classification Search
USPC .......................................................... 604/218
See application file for complete search history.

(56) References Cited

U.S. PATENT DOCUMENTS

| | | |
|---|---|---|
| 2016/0008541 A1 | 1/2016 | Hirschel et al. |
| 2018/0104414 A1* | 4/2018 | Karlsson ............. A61M 5/2033 |

FOREIGN PATENT DOCUMENTS

| | | |
|---|---|---|
| EP | 2918301 A1 | 9/2015 |
| JP | 2014-500089 A | 1/2014 |
| JP | 2016-512766 A | 5/2016 |
| TW | 201505681 A | 2/2015 |
| TW | 201709939 A | 3/2017 |
| WO | 2012/073032 A1 | 6/2012 |
| WO | 2014/154491 A1 | 10/2014 |
| WO | 2016/169748 A1 | 10/2016 |

\* cited by examiner

TRANSPORT ASSEMBLY FOR A MEDICAMENT DELIVERY DEVICE AND A MEDICAMENT DELIVERY DEVICE COMPRISING THE SAME

CROSS REFERENCE TO RELATED APPLICATIONS

The present application is a U.S. National Phase Application pursuant to 35 U.S.C. § 371 of International Application No. PCT/EP2018/067777 filed Jul. 2, 2018, which claims priority to European Patent Application No. 17180916.3 filed Jul. 12, 2017. The entire disclosure contents of these applications are herewith incorporated by reference into the present application.

TECHNICAL FIELD

The present disclosure generally relates to medical devices. In particular, it relates to a transport assembly for a medicament delivery device, to a medicament delivery device comprising a transport assembly and to a method of shipping components of a medicament delivery device for final assembly.

BACKGROUND

Medicament delivery devices, in particular automated administration devices such as auto-injectors, are typically spring-biased. A device of this type may be activated for example by pushing the device towards the injection site, whereby a delivery member cover is moved in the proximal direction further into the housing, causing the device activation, or by means of an external button or slider.

Medicament delivery devices of the above type may often be shipped as sub-assemblies to the site of final assembly. This is because the components of the medicament delivery device may be manufactured at a different location than the location of final assembly, where a medicament container containing the medicament is placed inside the housing of the medicament delivery device.

One of the sub-assemblies may comprise an administration assembly, or "power-pack", which for an automated injection device typically comprises a spring-biased component such as a plunger rod. The biasing force in the power-pack may be substantial to provide the required force to push the medicament out through the delivery member.

There is a risk that the power-pack fires off due to vibrations or impact during shipping. This may result in additional work to reload fired-off power-packs once the location of final assembly has been reached, or if reloading is not possible fired-off sub-assemblies may have to be discarded. There is additionally a risk that personnel may be injured if a power-pack is being fired off during handling of the sub-assemblies. One way to reduce the risk of personal injuries is to pack each sub-assembly in its own package for shipment, but this leaves a substantial spatial and environmental footprint and thus makes transport less efficient and more expensive.

SUMMARY

In view of the above, a general object of the present disclosure is to provide a transport assembly for a medicament delivery device which solves or at least mitigates problems of the prior art.

There is hence according to a first aspect of the present disclosure provided a transport assembly for shipping components of a medicament delivery device to final assembly, the transport assembly being configured to be mounted into a housing of a medicament delivery device, comprising: a plunger rod, a first resilient member configured to bias the plunger rod in the proximal direction, an elongated plunger rod holder configured to receive the plunger rod and configured to engage with the plunger rod to prevent the plunger rod from movement in the proximal direction, a transport securing sleeve configured to receive a portion of the plunger rod holder, and configured to move axially from a first position relative to the plunger rod holder in which the transport securing sleeve prevents the plunger rod holder to disengage from the plunger rod to a second position located distally relative to the first position, enabling disengagement of the plunger rod holder from the plunger rod, a rear end cap, and a second resilient member configured to bear against the rear end cap and configured to bias the transport securing sleeve in the proximal direction away from the second position.

Due to the proximally directed biasing of the transport securing sleeve, the transport securing sleeve is biased away from the second position preventing the plunger rod holder from disengaging from the plunger rod. Thus, as long as the transport securing sleeve is in such an axial position that it prevents disengagement, the plunger rod will not be fired off. The second resilient member hence protects from accidental firing of the plunger rod, which could otherwise have been triggered by vibrations or impact during transport of the transport assembly. There is hence a reduced risk of accidental triggering of the plunger rod during shipping.

According to one embodiment the rear end cap has a tubular body and the transport securing sleeve is configured to receive a portion of the tubular body, the transport securing sleeve being configured to be set in a transport position located proximally from the first position, the transport securing sleeve being configured to prevent the plunger rod holder from disengaging from the plunger rod in the transport position, and wherein in the transport position the transport securing sleeve is configured to engage with the tubular body to retain the transport securing sleeve in the transport position.

The transport securing sleeve is releasably engageable with the tubular body of the rear end cap. Under normal conditions, the transport securing sleeve will remain engaged with the tubular body when placed in the transport position. However, if sufficient force in the distal direction is applied to the transport securing sleeve, the transport securing sleeve will disengage from the tubular body. This is normally done when the transport assembly has reached the location of final assembly. The transport securing sleeve is here disengaged from the tubular body by moving it in the distal direction, whereby it attains its first position.

According to one embodiment the tubular body is provided with a radially outwards extending protrusion and the transport securing sleeve has a recess configured to receive the radially outwards extending protrusion in the transport position to retain the transport securing sleeve in the transport position.

According to one embodiment the radially outwards extending protrusion has a distal end face configured to prevent the transport securing sleeve to return to the transport position once the transport securing sleeve has been moved from the transport position to the first position.

The tubular body may hence be provided with a radially outwards extending protrusion, or transport securing sleeve lock, which prevents the transport securing sleeve from moving from the first position further in the proximal direction once it has been set in the first position.

According to one embodiment the second resilient member is a spring.

According to one embodiment the spring is a compression coil spring.

According to one embodiment the transport securing sleeve has a proximal portion having a first outer diameter and a distal portion located distally with respect to the proximal portion having a second outer diameter which is smaller than the first diameter, wherein a distal flange surface defines the transition from the distal portion to the proximal portion, and wherein the second resilient member is configured to bear against the distal flange surface to thereby bias the transport securing sleeve towards the first position.

According to one embodiment the rear end cap has an end flange surface and a tubular body extending proximally from the end flange surface, wherein the tubular body is configured to receive the plunger rod holder.

According to one embodiment the tubular body is configured to engage with the plunger rod holder to prevent relative axial movement between the plunger rod holder and the rear end cap.

According to one embodiment the plunger rod holder has a first hold and release structure and the plunger rod has a second hold and release structure, wherein in the first position the transport securing sleeve is configured to maintain the first hold and release structure in an axially locking contact position with the second hold and release structure in which the second hold and release structure is prevented from movement relative to the first hold and release structure, thereby locking the plunger rod axially relative to the plunger rod holder, wherein in the second position the transport securing sleeve is configured to allow the first hold and release structure to move from the axially locking contact position, whereby biasing of the plunger rod provided by the first resilient member causes the second hold and release structure to act with a proximally directed force on the first hold and release structure, moving the first hold and release structure from the axially locking contact position to thereby release the plunger rod from the plunger rod holder.

There is according to a second aspect of the present disclosure provided a medicament delivery device comprising: a housing, and a transport assembly as according to the first aspect, configured to be received by the housing.

There is according to a third aspect of the present disclosure provided a method of shipping components of a medicament delivery device for final assembly, wherein the method comprises: placing a plurality of transport assemblies according to the first aspect in a box.

According to one embodiment the transport assemblies are placed in direct contact with each other in the box.

One embodiment comprises prior to placing the plurality of transport assemblies in the box, setting each transport assembly in a transport mode by setting each transport securing sleeve in a transport position to engage with a respective rear end cap.

Generally, all terms used in the claims are to be interpreted according to their ordinary meaning in the technical field, unless explicitly defined otherwise herein. All references to "a/an/the element, apparatus, component, means, etc. are to be interpreted openly as referring to at least one instance of the element, apparatus, component, means, etc., unless explicitly stated otherwise.

BRIEF DESCRIPTION OF THE DRAWINGS

The specific embodiments of the inventive concept will now be described, by way of example, with reference to the accompanying drawings, in which.

DETAILED DESCRIPTION

The inventive concept will now be described more fully hereinafter with reference to the accompanying drawings, in which exemplifying embodiments are shown. The inventive concept may, however, be embodied in many different forms and should not be construed as limited to the embodiments set forth herein; rather, these embodiments are provided by way of example so that this disclosure will be thorough and complete, and will fully convey the scope of the inventive concept to those skilled in the art. Like numbers refer to like elements throughout the description.

In the present disclosure, when the term "distal direction" is used, this refers to the direction pointing away from the dose delivery site during use of the medicament delivery device. When the term "distal part/end" is used, this refers to the part/end of the delivery device, or the parts/ends of the members thereof, which under use of the medicament delivery device is/are located furthest away from the dose delivery site. Correspondingly, when the term "proximal direction" is used, this refers to the direction pointing towards the dose delivery site during use of the medicament delivery device. When the term "proximal part/end" is used, this refers to the part/end of the delivery device, or the parts/ends of the members thereof, which under use of the medicament delivery device is/are located closest to the dose delivery site.

Further, the terms "longitudinal", "longitudinally", "axially" and "axial" refer to a direction extending from the proximal end to the distal end and along the device or components thereof, typically in the direction of the longest extension of the device and/or component.

Similarly, the terms "transverse", "transversal" and "transversally" refer to a direction generally perpendicular to the longitudinal direction.

Figure 1:
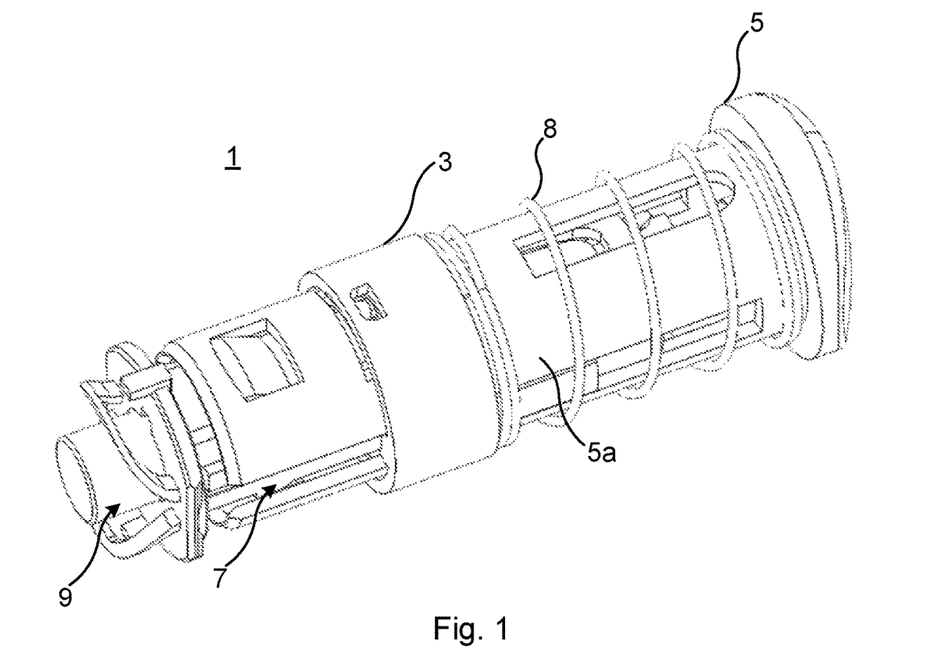
FIG. 1 is perspective view of an example of a transport assembly for a medicament delivery device.

FIG. 1 shows an example of a transport assembly 1 for a medicament delivery device. The transport assembly 1 is adapted to be shipped from the location of assembly to the location of final assembly of the medicament delivery device. Hereto, the transport assembly 1 is specifically adapted for reducing the risk of accidental firing off of a biased component contained therein, as will be described in more detail in what follows.

The transport assembly 1 comprises an essentially cylindrical transport securing sleeve 3 and a rear end cap 5 having a tubular body 5a configured to be received by the transport securing sleeve 3. The transport securing sleeve 3 is configured to be moved axially relative to the tubular body 5a. The transport assembly 1 further comprises an elongated plunger rod holder 7 configured to be received by the tubular body 5a, a plunger rod 9 configured to be received by the plunger rod holder 7, and a resilient member 8, in the following referred to as second resilient member 8, configured to bias the transport securing sleeve 3 in the proximal direction.

Figure 8:
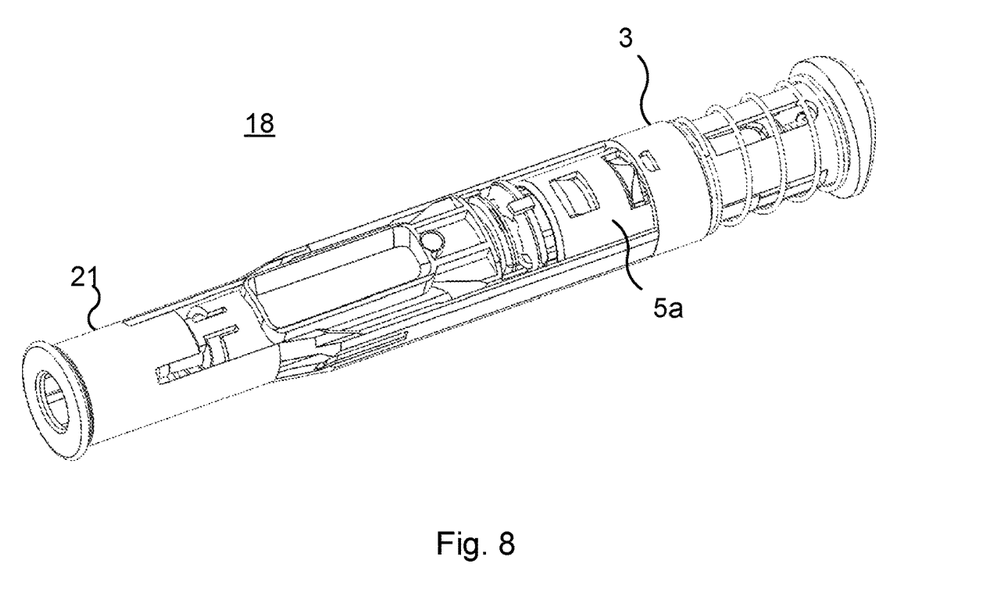
FIG. 8 shows the medicament delivery device in FIG. 7 with the housing removed to expose the interior of the medicament delivery device.

The transport assembly 1 is configured to be set in a transport mode depicted in FIG. 1, and in a medicament administration mode shown in FIG. 8. In the transport mode, the transport securing sleeve 3 is set in a transport position. In the transport position, the transport securing sleeve 3 engages with the tubular body 5a of the rear end cap 5. To set the transport assembly 1 in the medicament administration mode, the transport securing sleeve 3 is disengaged from the tubular body 5a by acting on it with a sufficiently high force in the distal direction. The transport securing sleeve 3 is thus set in a first position relative to the rear end cap 5. In the medicament administration mode the transport securing sleeve 3 is configured to be moved between the first position and a second position. The second position is located distally with respect to the first position. The second resilient member 8 is configured to bias the transport securing sleeve 3 in the proximal direction, away from the second position both in the transport mode and in the medicament administration mode. In the medicament administration mode, the second resilient member 8 is configured to bias the transport securing sleeve 3 towards the first position.

Figure 2:
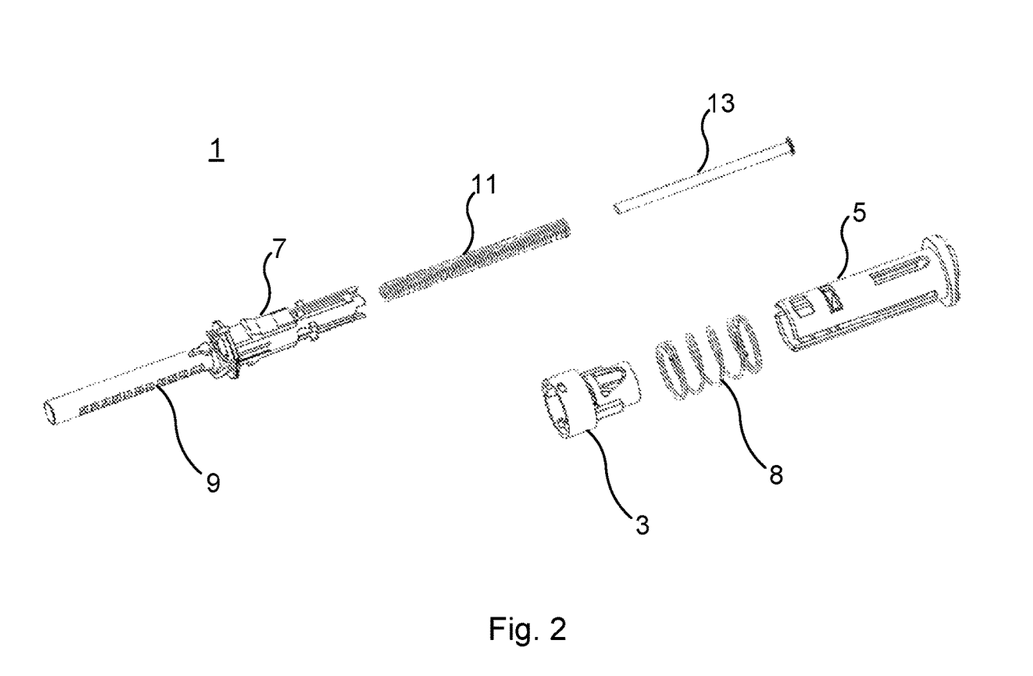
FIG. 2 depicts an exploded view of the transport assembly in FIG. 1.

FIG. 2 is an exploded view of the transport assembly 1. The transport assembly further comprises a first resilient member 11, for example a spring, a rod 13, and a second resilient member 15, for example a spring.

The plunger rod holder 7 is configured to receive the plunger rod 9. The plunger rod has 9 has an inner axial channel, not shown. The first resilient member 11 is configured to be received by the plunger rod 9. In particular, the first resilient member 11 is configured to be received in the axial channel of the plunger rod 9. The first resilient member 11 is configured to receive the rod 13 when arranged in the axial channel. Bending of the highly stiff first resilient member 11 can thus be prevented.

The plunger rod holder 7 is configured to engage with the plunger rod 9, to prevent movement of the plunger rod 9 in the proximal direction when the transport securing sleeve 3 is in the first position or in the transport position. The transport securing sleeve 3 encloses the plunger rod holder 7 and the plunger rod 9 circumferentially, and depending on the particular realisation of the transport securing sleeve 3, restricts tangential or radial movement of the plunger rod holder 7 in the first position and in the transport position. In the present example, the transport securing sleeve 3 is configured to restrict tangential movement of the plunger rod holder 7 when in the first position and in the transport position, as will be explained in more detail in what follows.

Figure 3:
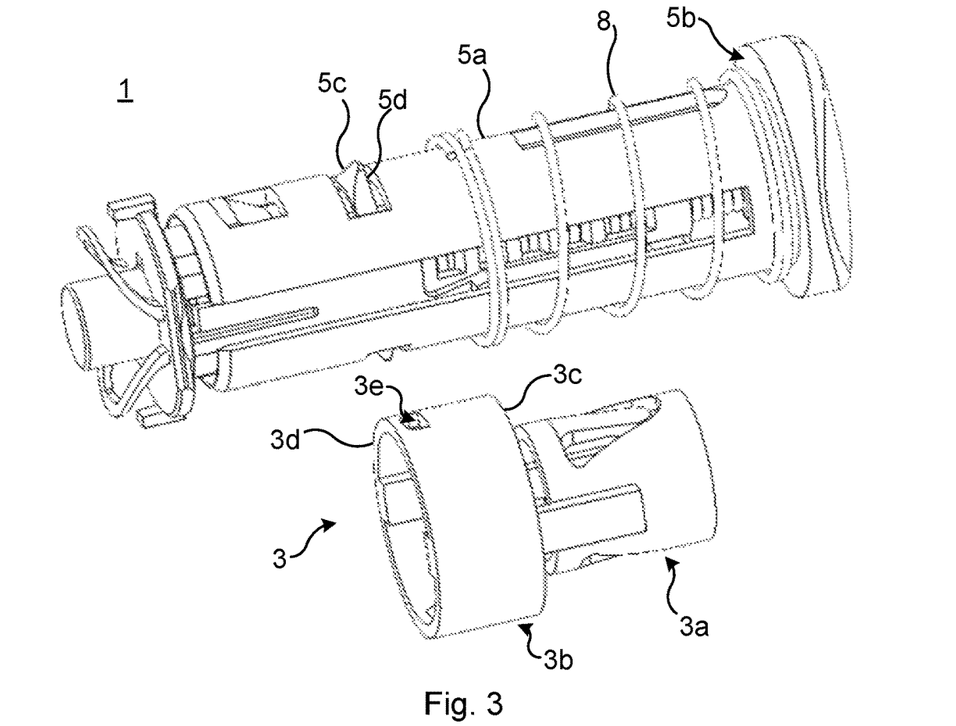
FIG. 3 is a perspective view of the transport assembly in FIG. 1 with a transport securing sleeve placed on the side of the main body of the transport assembly.

FIG. 3 shows the transport securing sleeve 3 removed from the tubular body 5a of the rear end cap 5. The transport securing sleeve 3 has a distal portion 3a and proximal portion 3b. The distal portion 3a has a smaller outer diameter than the proximal portion 3b. The transport securing sleeve 3 has a distal flange surface 3c which defines the transition between the distal portion 3a and the proximal portion 3b. The transport securing sleeve 3 also has a proximal flange surface 3d which defines a proximal face of the transport securing sleeve 3.

The rear end cap 5 has an end flange surface 5b. The second resilient member 8 is configured bear against the end flange surface 5b of the rear end cap 5 and against the distal flange surface 3c of the transport securing sleeve 3. The transport securing sleeve 3 is thus biased in the proximal direction by the second resilient member 8.

The transport securing sleeve 3 is furthermore configured to engage with the tubular body 5a of the rear end cap 5 when the transport securing sleeve 3 is in the transport position. Hereto, the transport securing sleeve 3 has a recess or opening 3e and the tubular body 5a has a radially outwards extending protrusion 5c configured to be received by the recess 3e. When the transport securing sleeve 3 is moved to the transport position, the radially outwards extending protrusion 5c engages with the recess 3e. The radially outwards extending protrusion 5c may be wedge-shaped or bevelled to allow for the transport securing sleeve 3 to disengage from the tubular body 5a if sufficient force is applied in the distal direction. Moreover, the radially outwards extending protrusion 5c has a distal end face 5d configured to prevent the transport securing sleeve 3 to return to the transport position once the transport securing sleeve 3 has been moved from the transport position to the first position.

Figure 4:
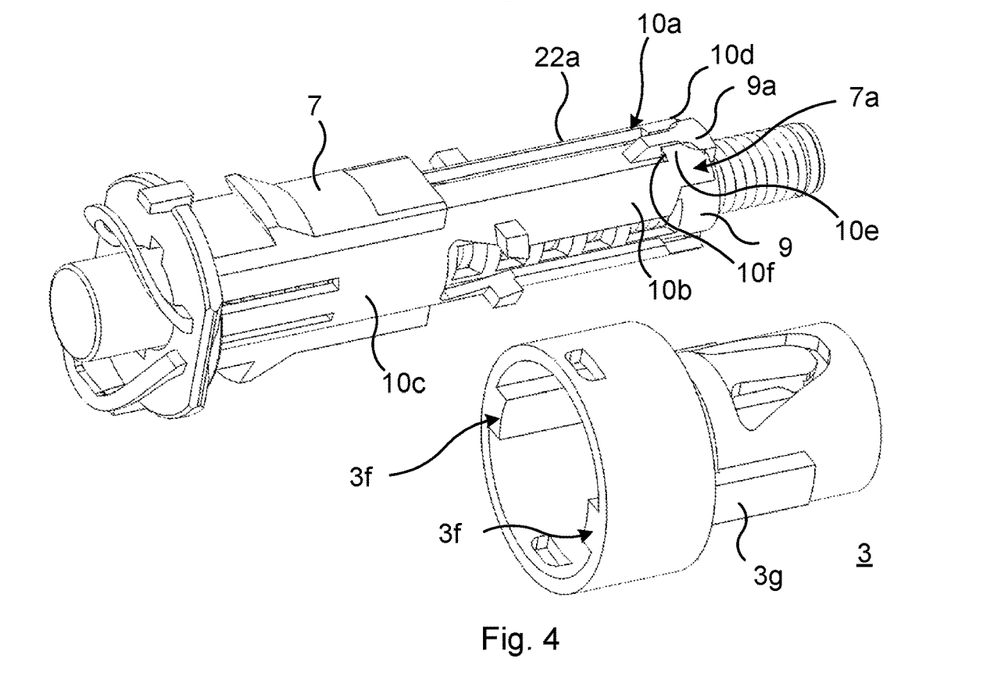
FIG. 4 is a perspective view of transport assembly in FIG. 1 with a rear end cap removed.

Turning now to FIG. 4 a perspective view of the plunger rod holder 7, the plunger rod 9 and the transport securing sleeve 3 are shown. The plunger rod 9 is received by the plunger rod holder 7. The exemplified plunger rod holder 7 has a first hold and release structure 7a, which comprises a first arm 10a and a second arm 10b extending parallel with each other. The first arm 10a and the second arm 10b extend in the distal direction from their attachment with a main body 10c of the plunger rod holder 7. Each of the first arm 10a and the second arm 10b has a tangential extension which is typically less than 90 degrees. To this end, the circumferential or tangential extension of each of the first arm 10a and the second arm 10b is typically less than one fourth of a turn in the circumferential direction of the plunger rod holder 7. The plunger rod holder 7 may for instance be provided with four arms in total, which is the case in the present example. Each arm, e.g. the first arm 10a and the second arm 10b, may be connected to the main body 10c of the plunger rod holder 7 by means of living hinges. Each of the first arm 10a, the second arm 10b, and the two remaining arms, may due to their slender nature be flexible in the tangential direction.

Although there may be in total four arms provided, only the first and the second arm 10a, 10b, which form a first arm pair, will be described in more detail in the following. The third and the fourth arm form a second arm pair. The structure of all the arms is the same.

The first arm 10a comprises a first tangential tab 10d and the second arm 10b comprises a second tangential tab 10e. The first and second tangential tabs 10d and 10e extend towards each other in the tangential direction. The tangential distance between the first arm 10a and the second arm 10b hence decreases between the two tangential tabs 10d and 10e.

The plunger rod 9 comprises a second hold and release structure 9a, which in the present example comprises a radially outward extending protrusion or wing. The first and second tangential tabs 10d and 10e are configured to cooperate with the radially outwards extending protrusion. In particular, two tangential tabs 10d and 10e are configured to block proximal movement of the radially outwards extending protrusion and thus of the plunger rod 9 when the transport securing sleeve 3 is in the first position or in the transport position. The distance between the two tangential tabs 10d and 10e is too small for the radially outwards extending protrusion to pass between. The plunger rod 9 is hence maintained in an axially locked position with the plunger rod holder 7 when the transport securing sleeve 3 is in the first position or in the transport position.

Figure 5:
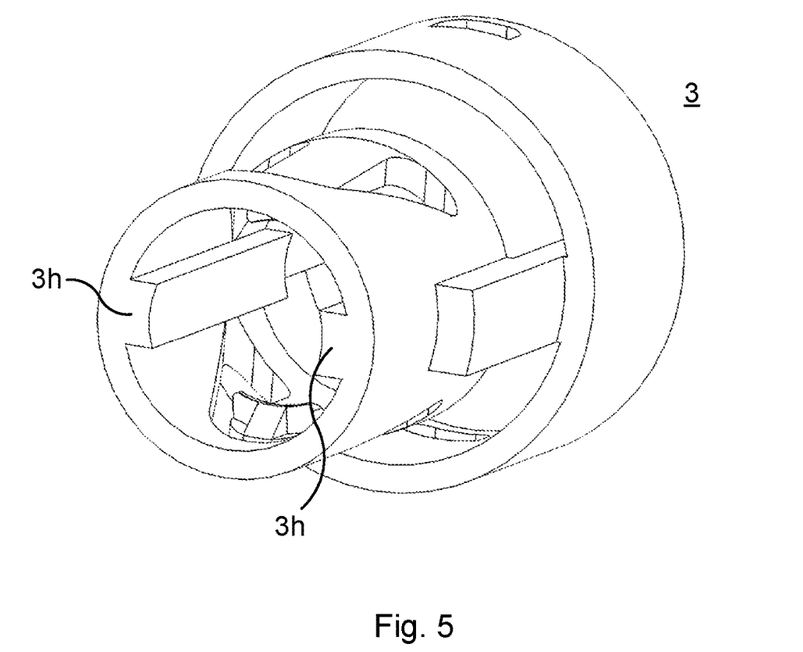
FIG. 5 shows a perspective view of the transport securing sleeve.

The transport securing sleeve 3 is tubular and has an inner surface provided with axially extending ribs 3f. Axially extending ribs 3h also are provided inside the distal portion 3a of the transport securing sleeve 3, as shown in FIG. 5. The axially extending ribs 3f and 3h are configured to run between the first arm pair and the second arm pair. In particular, the first arm 10a and the second arm 10b are prevented from tangential movement as long as the axially extending ribs 3h inside the distal portion 3a of the transport securing sleeve 3 run between the first arm pair and the second arm pair. Once these axially extending ribs 3h move distally beyond the first arm 10a and the second arm 10b and out from their position between the first arm pair and the second arm pair, when the transport securing sleeve 3 has been moved sufficiently in the distal direction from the first position towards the second position, the biasing of the plunger rod 9 and the contact between the radially outwards extending portion and the two tangential tabs 10d and 10e, will force the first arm 10a and the second arm 10b to move in the tangential direction. The inner diameter of the distal portion 3a cannot accommodate any substantial radial movement of the first arm 10a and the second arm 10b. The distance between the opposing first tangential tab 10d and the second tangential tab 10e will thus increase, allowing the radially outwards extending portion to pass between. The plunger rod 9 is thus released from engagement with the plunger rod holder 7.

The transport securing sleeve 3 also has outer axial ribs 3g configured to run in corresponding slots in the tubular body 5 of the rear end cap 5. The transport securing sleeve 3 is thereby prevented from rotation relative to the rear end cap 5. Since the transport securing sleeve 3 has the axially extending ribs 3f and 3h running between the first arm pair and the second arm pair of the plunger rod holder 7, the plunger rod holder 7 is also prevented to rotate relative to the rear end cap 5. Additionally, the plunger rod 9 is rotationally locked relative to the plunger rod holder 7 since the radially outwards extending protrusion is configured to run in the space between the first arm 10a and the second arm 10b. The radially outwards extending protrusion hence forms a guiding structure to prevent rotation of the plunger rod 9 relative to the plunger rod holder 7. All of the above-described components are hence prevented to rotate relative to the housing of the medicament delivery device in which they are mounted.

Figure 6:
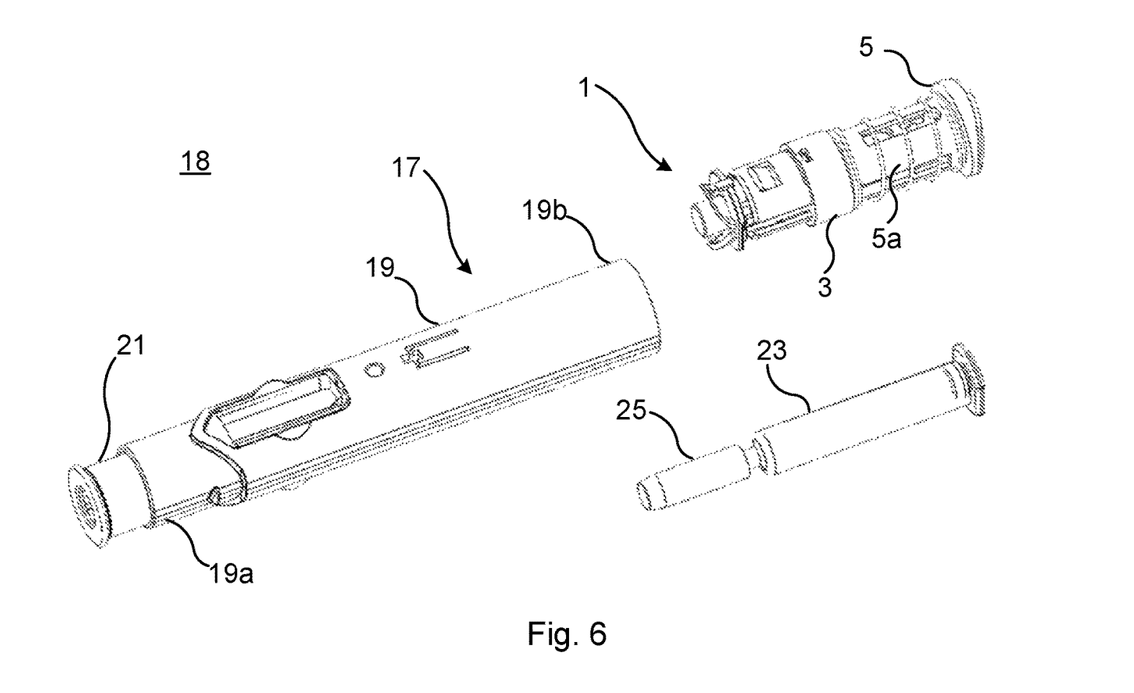
FIG. 6 shows a perspective view of various sub-assemblies of a medicament delivery device, including the transport assembly in FIG. 1.

FIG. 6 shows three sub-assemblies of a medicament delivery device 18, in the present example an auto-injector. A first of these sub-assemblies is the transport assembly 1 described above. The transport assembly 1 is here set in the transport mode with the transport securing sleeve 3 in the transport position engaging with the tubular body 5a of the rear end cap 5.

A second sub-assembly 17 includes a housing 19 having a proximal end 19a and a distal end 19b, a delivery member cover 21 extending from a proximal opening in the proximal end 19a of the housing 19, and a medicament container holder, not shown.

In a fully assembled state of the medicament delivery device 18, the delivery member cover 21 is biased in the proximal direction. The delivery member cover 21 is configured to be moved linearly, or axially, relative to the housing 19. The delivery member cover 21 is configured to be moved between an extended position relative to the housing 19, shown in FIG. 6, and a retracted position relative to the housing 19. In the retracted position, a greater portion of the delivery member cover 21 is received by the housing 19 than in the extended position. The delivery member cover 21 is configured to be biased towards the extended position. In particular, the delivery member cover 21 has a distal end which is configured to cooperate with the proximal flange surface 3d of the transport securing sleeve 3. Movement of the delivery member cover 21 from the extended position towards the retracted position hence causes the transport securing sleeve 3 to move from the first position towards the second position.

The third sub-assembly depicted in FIG. 6 includes a medicament container 23 provided with a delivery member and including a medicament, a stopper arranged in the medicament container and configured to be moved linearly inside the medicament container by the plunger rod 9, and a delivery member shield 25.

Typically, when performing final assembly of the medicament delivery device 18, the third sub-assembly, which includes the medicament container 23, is placed inside the housing 19 through a distal opening at the distal end 19b of the housing 19. The transport assembly 1 is set in the medicament administration mode from the transport mode by moving the transport securing sleeve 3 in the distal direction so that it disengages from the tubular body 5a of the rear end cap 5. Finally, the transport assembly 1 is mounted in the housing 19 through the distal opening at the distal end 19b.

Figure 7:
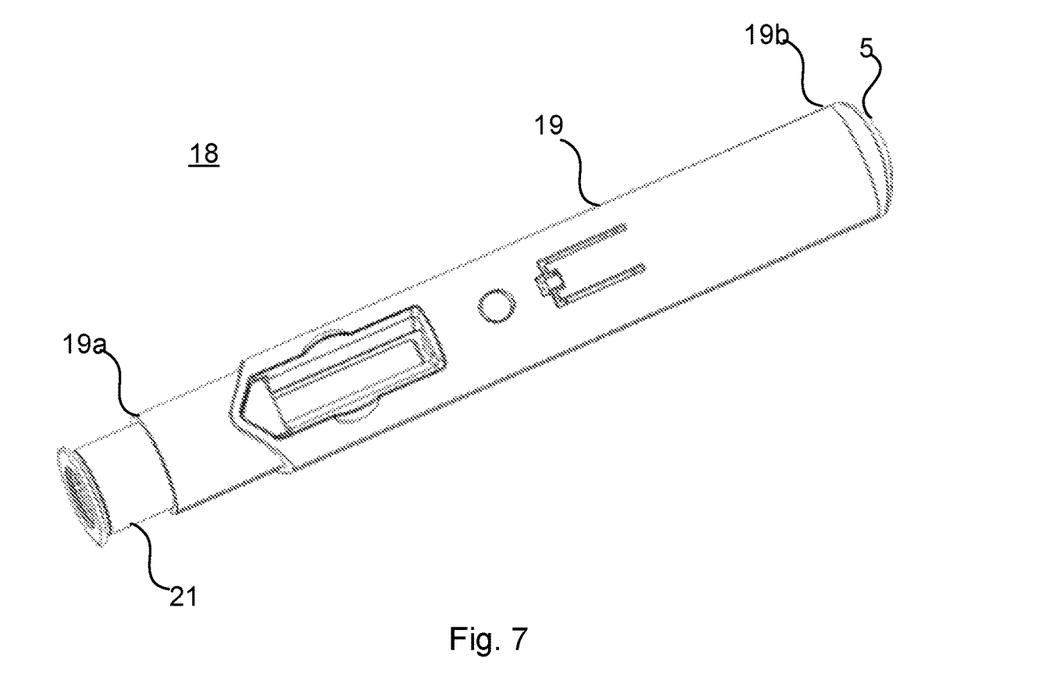
FIG. 7 is a perspective view of a medicament delivery device comprising the transport assembly in FIG. 1.

The fully assembled medicament delivery device 18 is shown in FIG. 7. FIG. 8 shows the medicament delivery device 18 with the housing 19 removed. Here, it can be seen that the transport securing sleeve 3 is in the first position, which is located distally with respect to the transport position shown in FIG. 1.

Figure 9:
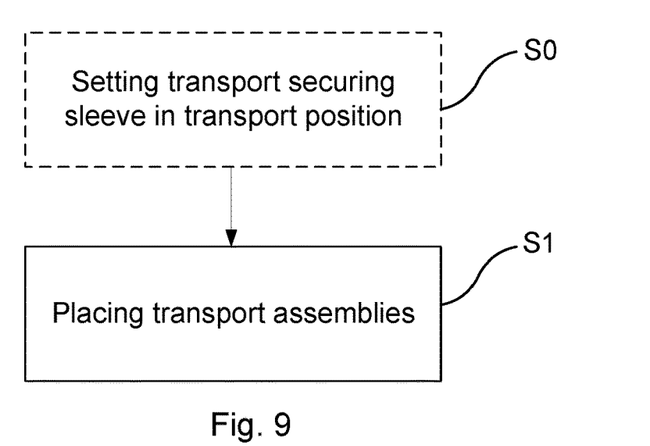
FIG. 9 is a flowchart of a method of shipping components of a medicament delivery device for final assembly.

FIG. 10 shows a flowchart of a method of shipping components of the medicament delivery device 18. First, when the components of the transport assembly 1 have been manufactured, they are assembled, for example by means of pick and place robots. During the assembly, in a step S0 the transport securing sleeve 3 of each transport assembly 1 may be set in the transport position. The transport securing sleeve 3 thus engages with the tubular body 5a of the rear end cover 5. Next, in a step S1 a plurality of transport assemblies 1, each being set in the transport mode are placed inside a box. Since the risk of accidental firing of the plunger rod 9 is reduced by means of the forward biasing provided by the second resilient member 8 onto the transport securing sleeve 3 and due to the engagement between the transport securing sleeve 3 and the tubular body 5a, the box can be filled with a plurality of transport assemblies 1, placed in direct contact with each other. The transport assemblies 1 may for example be placed one after the other and/or stacked in several layers on top of each other in the box.

Figure 10A:
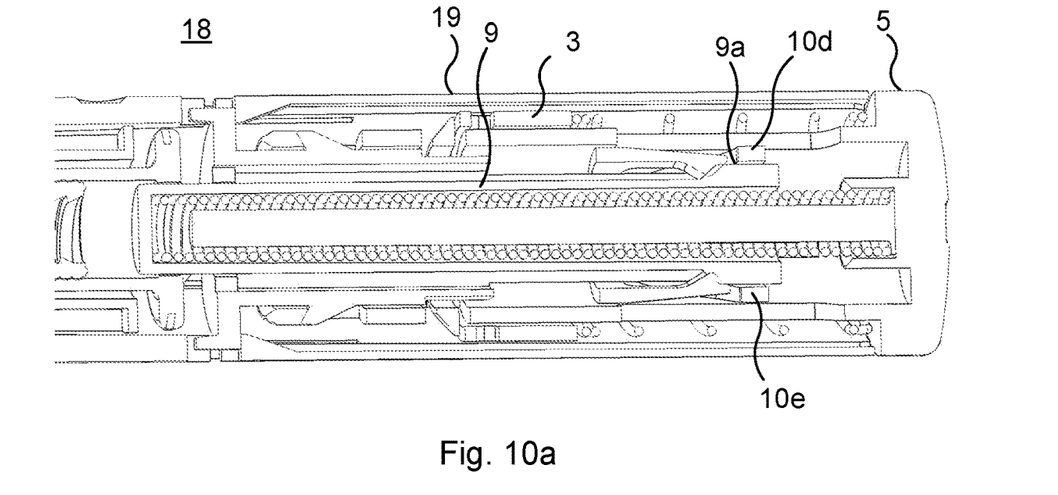
FIG. 10a shows longitudinal sections of the medicament delivery device in FIG. 7 in a stage of medicament administration.

To illustrate an example of engagement and disengagement between the plunger rod holder 7 and the plunger rod 9, the operation of the fully assembled medicament delivery device 18 will now be described with reference to FIGS. 10a-10c.

In FIG. 1a a longitudinal section of a distal end portion of the medicament delivery device 18 comprising the transport assembly 1 is shown. The transport securing sleeve 3 is in the first position and the axially extending ribs 3h are provided between the first arm pair and the second arm pair, preventing e.g. the first arm 10a and the second arm 10b from moving in the tangential direction. The second hold end release structure 9a, including the radially outwards extending protrusion is thus not able to move past the two distal end tangential extending portions 10d and 10e.

Figure 10B:
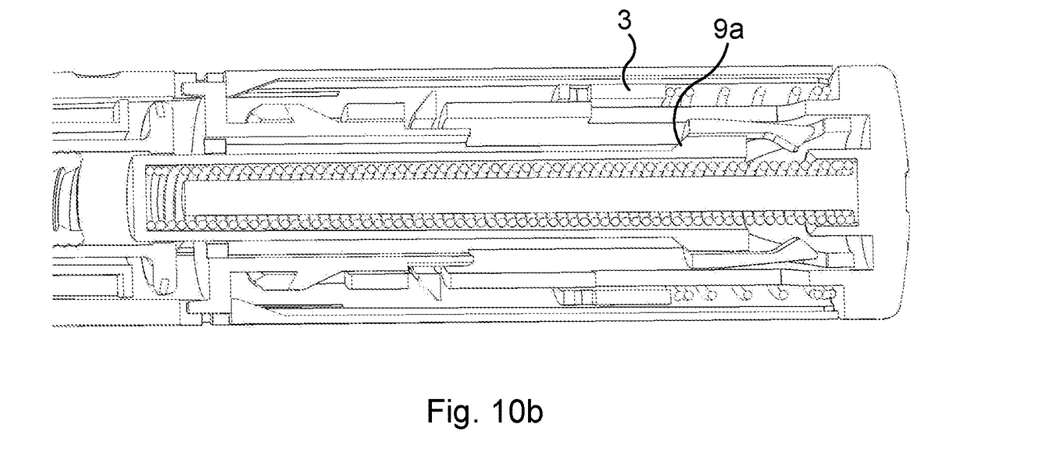
FIG. 10b shows longitudinal sections of the medicament delivery device in FIG. 7 in another stage of medicament administration.

In FIG. 10b the transport securing sleeve 3 has been moved in the distal direction towards the second position by the delivery member cover, which cannot be seen in this longitudinal section. The transport securing sleeve 3 has been moved to an activation position, which is where the axially extending ribs 3h of the distal portion 3a move out from between the first arm pair and the second arm pair. This allows the hinged first arm 10a and the second arm 10b to move tangentially, due to the force acting thereon by the biased radially outwards extending portion of the plunger rod 9.

Figure 10C:
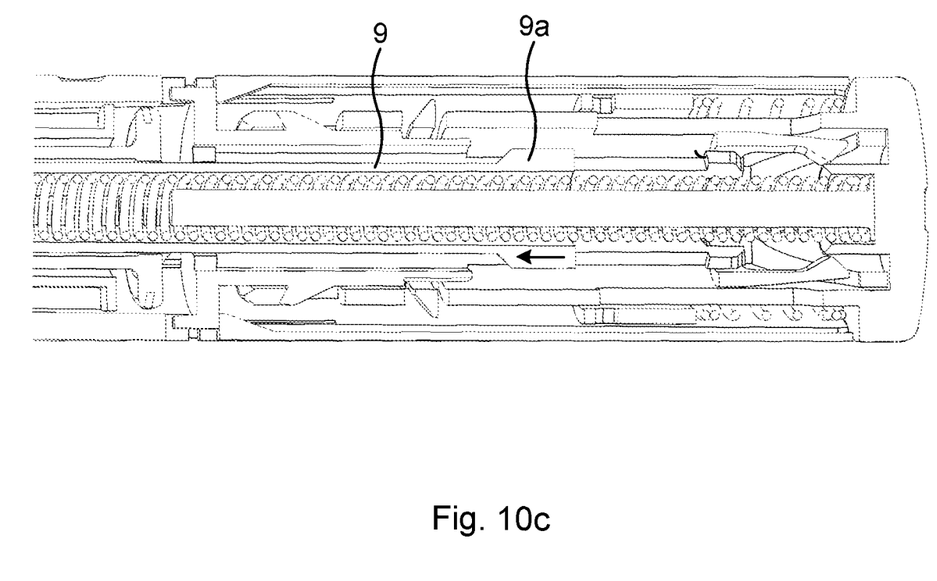
FIG. 10c shows longitudinal sections of the medicament delivery device in FIG. 7 in yet another stage of medicament administration.

In FIG. 10c the transport securing sleeve 3 is in the second position, the first arm 10a and the second arm 10b have been moved in the tangential direction and the plunger rod 9 has thus been released from being axially locked with the plunger rod holder 7. The plunger rod 9 has in particular been moved in the proximal direction as indicated by the arrow.

The inventive concept has mainly been described above with reference to a few examples. However, as is readily appreciated by a person skilled in the art, other embodiments than the ones disclosed above are equally possible within the scope of the inventive concept, as defined by the appended claims.

The invention claimed is:

1. A transport assembly for shipping components of a medicament delivery device to final assembly, the transport assembly being configured to be mounted into a housing of a medicament delivery device, the transport assembly comprising:
    a plunger rod,
    a first resilient member configured to bias the plunger rod in a proximal direction,
    an elongated plunger rod holder configured to receive the plunger rod and configured to engage with the plunger rod to prevent the plunger rod from movement in the proximal direction,
    a transport securing sleeve configured to receive a portion of the plunger rod holder, and configured to move axially from a first position relative to the plunger rod holder in which the transport securing sleeve prevents the plunger rod holder from disengaging from the plunger rod to a second position located distally relative to the first position, where in the second position the plunger rod holder will disengage from the plunger rod,
    a rear end cap, and
    a second resilient member configured to bear against the rear end cap, where the second resilient member biases the transport securing sleeve in the proximal direction away from the second position,
    wherein the transport securing sleeve has a proximal portion having a first outer diameter and a distal portion located distally with respect to the proximal portion having a second outer diameter which is smaller than the first diameter, wherein a distal flange surface defines the transition from the distal portion to the proximal portion, and wherein the second resilient member is configured to bear against the distal flange surface to thereby bias the transport securing sleeve towards the first position.

2. The transport assembly as claimed in claim 1, wherein the rear end cap has a tubular body and the transport securing sleeve is configured to receive a portion of the tubular body, the transport securing sleeve being configured to be set in a transport position located proximally from the first position, the transport securing sleeve being configured to prevent the plunger rod holder from disengaging from the plunger rod in the transport position, and wherein in the transport position the transport securing sleeve is configured to engage with the tubular body to retain the transport securing sleeve in the transport position.

3. The transport assembly as claimed in claim 2, wherein the tubular body is provided with a radially outwards extending protrusion and the transport securing sleeve has a recess configured to receive the radially outwards extending protrusion in the transport position to retain the transport securing sleeve in the transport position.

4. The transport assembly as claimed in claim 2, wherein the radially outwards extending protrusion has a distal end face configured to prevent the transport securing sleeve from returning to the transport position once the transport securing sleeve has been moved from the transport position to the first position.

5. The transport assembly as claimed in claim 4, wherein the spring is a compression coil spring.

6. The transport assembly as claimed in claim 1, wherein the second resilient member is a spring.

7. The transport assembly as claimed in claim 1, wherein the rear end cap has an end flange surface and a tubular body extending proximally from the end flange surface, wherein the tubular body is configured to receive the plunger rod holder.

8. The transport assembly as claimed in claim 7, wherein the tubular body is configured to engage with the plunger rod holder to prevent relative axial movement between the plunger rod holder and the rear end cap.

9. The transport assembly as claimed in claim 1, wherein the plunger rod holder has a first hold and release structure and the plunger rod has a second hold and release structure, wherein in the first position the transport securing sleeve is configured to maintain the first hold and release structure in an axially locking contact position with the second hold and release structure in which the second hold and release structure is prevented from movement relative to the first hold and release structure, thereby locking the plunger rod axially relative to the plunger rod holder,
    wherein in the second position the transport securing sleeve is configured to allow the first hold and release structure to move from the axially locking contact position, whereby biasing of the plunger rod provided by the first resilient member causes the second hold and release structure to act with a proximally directed force on the first hold and release structure, moving the first hold and release structure from the axially locking contact position to thereby release the plunger rod from the plunger rod holder.

10. A medicament delivery device comprising:
a housing, and
a transport assembly as claimed in claim 1 configured to be received by the housing.

11. A method of shipping components of a medicament delivery device for final assembly, wherein the method comprises:
placing a plurality of transport assemblies as claimed in claim 1 in a box.

12. The method as claimed in claim 11, wherein the plurality of transport assemblies are placed in direct contact with each other in the box.

13. The method as claimed in claim 11, comprising prior to placing the plurality of transport assemblies in the box, setting each transport assembly in a transport mode by setting each transport securing sleeve in a transport position to engage with a respective rear end cap.

14. A transport assembly comprising:
a plunger rod;
a first resilient member engaged with the plunger rod such that the plunger rod is biased in a proximal direction;
an elongated plunger rod holder surrounding and engaged with the plunger rod to prevent the plunger rod from moving axially in the proximal direction;
a rear end cap having a tubular body extending in the proximal direction;
a transport securing sleeve having a distal portion positioned within the tubular body and having a proximal portion configured to receive a portion of the plunger rod holder, where the transport securing sleeve is configured to move axially from a first position relative to the plunger rod holder to a second position located distally relative to the first position, where in the second position the plunger rod holder will disengage from the plunger rod; and
a second resilient member that engages the rear end cap and the proximal portion of the transport securing sleeve such that the transport securing sleeve is biased in the proximal direction when in the first and second positions,
wherein a distal flange surface defines the transition from the distal portion to the proximal portion, and wherein the second resilient member is configured to bear against the distal flange surface to thereby bias the transport securing sleeve towards the first position.

15. The transport assembly of claim 14, wherein the second resilient member bears against an end flange surface of the rear end cap.

16. The transport assembly of claim 14, wherein the transport securing sleeve is engaged with the tubular body of the rear end cap when the transport securing sleeve is in the first position.

17. The transport assembly of claim 14, wherein the transport securing sleeve encloses the plunger rod holder and the plunger rod circumferentially and restricts tangential or radial movement of the plunger rod holder when in the first and second positions.

18. The transport assembly of claim 14, wherein the transport securing sleeve has a recess or opening that engages a protrusion on the tubular body when the transport securing sleeve is in the first position.

19. The transport assembly of claim 18, wherein the protrusion disengages from the recess or opening when the transport securing sleeve is moved in a distal direction.

* * * * *